US012644054B2

(12) United States Patent
Nieminen et al.

(10) Patent No.: US 12,644,054 B2
(45) Date of Patent: Jun. 2, 2026

(54) METHOD AND PROCESS ARRANGEMENT FOR PRODUCING HYDROCARBONS

(71) Applicant: TEKNOLOGIAN TUTKIMUSKESKUS VTT OY, Espoo (FI)

(72) Inventors: Matti Nieminen, Vtt (FI); Matti Reinikainen, Vtt (FI)

(73) Assignee: TEKNOLOGIAN TUTKIMUSKESKUS VTT OY, Espoo (FI)

( * ) Notice: Subject to any disclaimer, the term of this patent is extended or adjusted under 35 U.S.C. 154(b) by 214 days.

(21) Appl. No.: 18/683,032

(22) PCT Filed: Aug. 9, 2022

(86) PCT No.: PCT/FI2022/050518
§ 371 (c)(1),
(2) Date: Feb. 12, 2024

(87) PCT Pub. No.: WO2023/017210
PCT Pub. Date: Feb. 16, 2023

(65) Prior Publication Data
US 2024/0352336 A1      Oct. 24, 2024

(30) Foreign Application Priority Data
Aug. 13, 2021      (FI) ...................................... 20215851

(51) Int. Cl.
*C10G 1/10*           (2006.01)
*C07C 4/22*           (2006.01)
(Continued)

(52) U.S. Cl.
CPC .................. *C10G 1/10* (2013.01); *C07C 4/22* (2013.01); *C08J 11/14* (2013.01); *C10G 1/002* (2013.01);
(Continued)

(58) Field of Classification Search
CPC .. C10G 1/10; C10G 1/002; C10G 2300/1003; C10G 2400/20; C10G 2400/30; C07C 4/22; C08J 11/14; C08J 2325/06
See application file for complete search history.

(56) References Cited

U.S. PATENT DOCUMENTS 11,851,622 B1 * 12/2023 Akah .......................... C10J 3/00
11,905,477 B2 * 2/2024 Nieminen ................ C10J 3/482
(Continued)

FOREIGN PATENT DOCUMENTS

| WO | 20050061673 A1 | 7/2005 |
| WO | 2020169888 A1 | 8/2020 |
| WO | 2020252228 A1 | 12/2020 |

OTHER PUBLICATIONS

International Search report for PCT/FI2002/050518, prepared by the European Patent Office, mailing date Nov. 4, 2022, 4 pages.

*Primary Examiner* — Ellen M Mcavoy
(74) *Attorney, Agent, or Firm* — Brooks Kushman P.C.

(57) ABSTRACT

A method and a process arrangement for producing hydrocarbons from plastic-based raw material by a gasification in an integrated process The integrated process includes a gasification unit for forming a gasification product, a steam cracking unit for forming a cracking product and a recovery unit for recovering hydrocarbons. The plastic-based raw material is gasified with steam in the gasification unit having at least one fluidized bed gasifier and the gasification product is formed, the gasification product is cooled at least partly for slowing and/or stopping the chemical reactions after the gasification, The gasification product is supplied to a quench tower of the gasification unit in which the gasification product is treated and condensable components are removed from the gasification product forming a treated gasification product, and the treated gasification product and the cracking product of the steam cracking unit are supplied
(Continued)

to the recovery unit for separating and recovering hydrocarbons.

16 Claims, 1 Drawing Sheet

(51) Int. Cl.
   *C08J 11/14*          (2006.01)
   *C10G 1/00*          (2006.01)
(52) U.S. Cl.
   CPC ...  *C08J 2325/06* (2013.01); *C10G 2300/1003*
          (2013.01); *C10G 2400/20* (2013.01); *C10G*
                                    *2400/30* (2013.01)

(56)                References Cited

U.S. PATENT DOCUMENTS

| | | | |
|---|---|---|---|
| 2008/0230444 | A1 | 9/2008 | Iwadate et al. |
| 2019/0161683 | A1 | 5/2019 | Narayanaswamy et al. |
| 2023/0312436 | A1* | 10/2023 | Nieminen .............. B01D 46/00 |
| | | | 585/241 |
| 2024/0158699 | A1* | 5/2024 | Nieminen ................. C10J 3/82 |

* cited by examiner

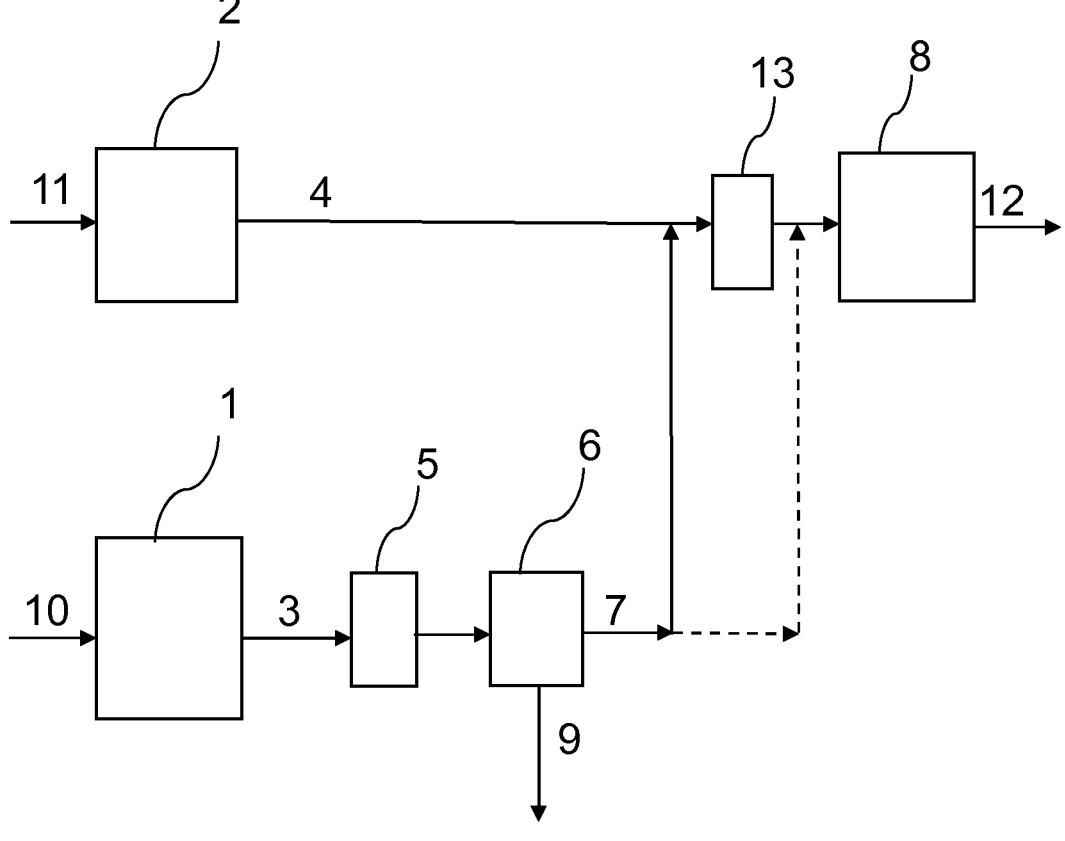

METHOD AND PROCESS ARRANGEMENT FOR PRODUCING HYDROCARBONS

CROSS-REFERENCE TO RELATED APPLICATION

This application is the U.S. national phase of PCT Application No. PCT/FI2022/050518 filed on Aug. 9, 2022, which claims priority to FI patent application No. 20215851 filed on Aug. 13, 2021, the disclosures of which are incorporated in their entirety by reference herein.

FIELD

The application relates to a method and a process arrangement for producing hydrocarbons from plastic-based raw material. Further, the application relates to a use of the method.

BACKGROUND

Known from the prior art is to produce olefins from fossil raw material by a cracking process, such as by a steam cracking process. Further, typical steam cracking process sites are fully constructed, and it might be difficult to arrange additional processes in these sites.

Further, it is known from the prior art that waste comprising mixed plastics is difficult to recycle and to utilize as raw material in new products.

OBJECTIVE

The objective is to solve the above problems. Especially, the objective is to improve an integrated process comprising a gasification unit and a steam cracking unit. Further, the objective is to recover olefins from polyolefin plastic waste and to recycle plastics. Further, the objective is to recycle polystyrene together with other plastic waste.

SUMMARY

The method and process arrangement and use are characterized by what are presented in the claims.

In the method and process arrangement, hydrocarbons are produced from plastic-based raw material by means of a gasification in an integrated process, in which the integrated process comprises at least one gasification unit for forming a gasification product, at least one cracking unit for forming a cracking product and at least one recovery unit for recovering hydrocarbons. The plastic-based raw material is gasified in the gasification unit to form the gasification product, the gasification product and the cracking product are supplied to the recovery unit for separating and recovering desired hydrocarbons.

BRIEF DESCRIPTION OF THE DRAWING

The accompanying drawing, which is included to provide a further understanding of the invention and constitutes a part of this specification, illustrates some embodiments of the invention and together with the description help to explain the principles of the invention. In the drawing:

FIG. 1 is a flow chart illustration of a process according to one embodiment.

DETAILED DESCRIPTION

In the method hydrocarbons are produced from plastic-based raw material, e.g. from waste material, by means of a gasification in an integrated process, in which the integrated process comprises at least one gasification unit for forming a gasification product, at least one steam cracking unit for forming a cracking product and at least one recovery unit for recovering hydrocarbons. The method comprises gasifying the plastic-based raw material with steam in the gasification unit comprising at least one fluidized bed gasifier and forming the gasification product, cooling at least partly the gasification product for slowing and/or stopping the chemical reactions after the gasification, supplying the gasification product to a quench tower of the gasification unit in which the gasification product is treated and condensable components are removed from the gasification product for forming a treated gasification product, pressurizing the treated gasification product, and supplying the treated gasification product and the cracking product of the steam cracking unit to the recovery unit for separating and recovering desired hydrocarbons. The desired hydrocarbons may comprise different hydrocarbons and one or more hydrocarbon fractions.

A process arrangement, i.e. an apparatus, for producing hydrocarbons from plastic-based raw material by means of a gasification in an integrated process, in which the integrated process comprises at least one gasification unit for forming a gasification product, at least one steam cracking unit for forming a cracking product and at least one recovery unit for recovering hydrocarbons, comprises the gasification unit comprising at least one fluidized bed gasifier for gasifying the plastic-based raw material with steam and for forming the gasification product, at least one cooling device for cooling at least partly the gasification product for slowing and/or stopping the chemical reactions after the gasification, at least one quench tower of the gasification unit into which the gasification product is supplied and in which the gasification product is treated and condensable components are removed from the gasification product for forming a treated gasification product, at t least one device for pressurizing the treated gasification product, and means for supplying the treated gasification product and the cracking product of the steam cracking unit to the recovery unit in order to separate and recover desired hydrocarbons.

Some embodiments of the method and the process arrangement are shown in FIG. 1.

In the integrated process, at least one gasification unit comprising the gasifier or gasifiers is interconnected to the steam cracking unit, e.g. an olefin cracking unit. Usually, the steam cracking unit comprises at least one cracking furnace. Further, the steam cracking unit may comprise at least one quench column and at least one transfer line for supplying the feed to the quench column. Further, the steam cracking unit may comprise at least one cooling device to cool the cracking product before the quench column. Typically, the process conditions of the outlet of the gasification unit, e.g. before the recovery unit, must meet the requirements at the steam cracking unit. In one embodiment, pressure is typically low 1-3 bar (g) and temperature around 200-250° C. In one embodiment, the treated gasification product is pressurized, when condensable components have been removed from the gasification product, e.g. after the quench tower of the gasification unit. In one embodiment, pressure of the treated gasification product is 1-3 bar, in one embodiment about 2-3 bar. Then back pressure of the cracking product stream can be won, and thus combining of the treated gasification product to the cracking product can be facilitated, i.e. the treated gasification product is pressurized against back pressure of the cracking product. In one embodiment, the treated gasification product is pressurized, and pressure of the treated gasification product is 1-3 bar. In one embodiment, the pressurization is performed by a compressor or other suitable device.

In this context, the gasification in the gasification unit means any gasification process by steam. In this context, the gasification may mean gasification and/or pyrolysis, and the gasifier may mean gasifier and/or pyrolyzer. The gasification is a process that converts raw material into gasification products, e.g. plastic-based raw material is chemically recycled back to virgin-like olefins. This is achieved by treating the raw material at suitable temperatures, with a controlled amount of steam. In one embodiment, the gasification is carried out at 680-750° C. Any suitable gasifier may be used in the gasification unit. In one embodiment, the fluidized bed gasifier is selected from a bubbling fluidized bed gasifier or a circulating fluidized bed gasifier.

In this context, the plastic-based raw material means any plastic mixture, waste material or the like which may comprise one or more polymers. The plastic-based raw material may comprise recycled plastics. The plastic-based raw material may comprise polyolefins, e.g. polyethylene or polypropylene, and other polymers, and further other components, such as paper, cardboard and/or aluminium material. In one embodiment, the plastic-based raw material may comprise also PVC plastic. The gasification product may be formed from polyolefins and/or recycled plastics in the gasification unit.

In this context, the gasification product means any product, flow, gas or the like, formed in the gasification unit. In one embodiment, the gasification product is gas. The gasification product comprises olefins, e.g. ethylene and propylene, and the gasification product may be rich in olefins. Further, the gasification product may comprise aromatics, e.g. benzene and toluene, and other hydrocarbons, e.g. butadiene. Usually, the gasification product is a mixture of hydrocarbons.

In the steam cracking unit, the cracking product is formed. In one embodiment, the steam cracking unit comprises at least one steam cracking furnace. The reactions may be carried out, for example at 750-900° C. in the steam cracking unit, such as in a steam cracking furnace, in which reaction time is short, e.g. below 1 second. For example, in a gasifier of the gasification unit, the residence time may be below 10 seconds, in one embodiment 1-10 seconds and in one embodiment below 4 seconds.

In this context, the cracking product means any product, flow, gas or the like formed in the steam cracking unit. In one embodiment, the cracking product is gas. The cracking product comprises olefins, and typically the cracking product is rich in olefins. Further, the cracking product may comprise other hydrocarbons and/or components.

In one embodiment, the gasification product is cooled rapidly to temperature which is below 640° C. after the gasification in order to stop chemical reactions. In one embodiment, reactions are killed rapidly after the gasification by cooling the gasification product to temperature of below 600° C., in one embodiment below 550° C., in order to stop chemical reactions. Then the yield of targeted products, e.g. light olefins, may be increased or maximised. In one embodiment, the process arrangement comprises at least one water quench or heat exchanger as the cooling device for cooling the gasification product after the gasification.

The gasification product is supplied to the quench tower of the gasification unit where the gasification product is treated and where condensable components are removed from the gasification product for forming the treated gasification product, and where simultaneously the gasification product is cooled. Then, the treated gasification product from the gasification unit can be transferred safely by pipeline. Any suitable quench tower can be used as the quench tower of the gasification unit. In one embodiment, the process arrangement comprises at least one gas transfer line to supply the gasification product to the quench tower of the gasification unit.

In this context, the condensable component means any condensable compound, agent or substance which is condensed from the gasification product. In one embodiment, the condensable components comprise tars. In one embodiment, the condensable components may comprise aromatics, styrenes or their combinations.

In one embodiment, at least tars are separated and removed from the gasification product in the quench tower of the gasification unit. After the quench tower the gasification product is clean of condensable compounds, e.g. tars. Then the tar-free gasification product can be supplied to the recovery unit. The tars might prevent transferring the gasification product longer distances, because tars in the gasification product can condense on the walls of the pipelines and finally clog the pipelines. When the gasification product is cleaned of condensable components and simultaneously is cooled in the quench tower, the gasification product can be transferred safely.

In one embodiment, the plastic-based raw material comprises polystyrene and/or styrene, and condensable components comprising styrene are recovered in the quench tower of the gasification unit. Then, polystyrene can be recycled together with polyolefins. In the gasification unit, the polystyrene is decomposed to styrene which is condensable component. The styrene can be recovered from the gasification product. Further, if the gasification product would be combined with the cracking product having a huge flow volume without the recovery of condensable components from the gasification product, styrene is diluted to so low level that it cannot be recovered from the product.

In one embodiment, the condensable components are recovered in the quench tower of the gasification unit. In one embodiment, the process arrangement comprises a recovery device, e.g. in connection with the quench tower of the gasification unit. In one embodiment, the quench tower of the gasification unit comprises at least a condensing part, e.g. a condensing device, and a recovery part, e.g. a recovery device.

In one embodiment, the treated gasification product and the cracking product of the steam cracking unit are supplied to a main quench tower. In one embodiment, the process arrangement comprises the main quench tower to which the treated gasification product and the cracking product of the steam cracking unit are supplied. In one embodiment, the treated gasification product and the cracking product of the steam cracking unit are combined and after that supplied to the main quench tower.

In one embodiment, the cracking product is treated in a main quench tower after the steam cracking. In one embodiment, the process arrangement comprises the main quench tower to which the cracking product of the steam cracking unit is supplied and in which the cracking product is treated. In one embodiment, the steam cracking unit comprises the main quench tower in which the cracking product is treated. Then, the treated gasification product is not treated in the main quench tower. In one embodiment, the cracking product of the steam cracking unit is supplied to the main quench tower, and the treated gasification product is combined with the cracking product of the steam cracking unit after the main quench tower.

In one embodiment, the treated gasification product and the cracking product are combined before the recovery unit to form a feed of the recovery unit. In one embodiment, the cracking product which is treated in a main quench tower and the treated gasification product are combined before the recovery unit to form the feed of the recovery unit. In one embodiment, the treated gasification product and the cracking product are combined to form the feed of the recovery unit, and the feed is supplied to a main quench tower and from the main quench tower to the recovery unit. In one embodiment, the treated gasification product and the cracking product are combined to form the feed of the recovery unit, and the feed is supplied to a main quench tower of the recovery unit. In one embodiment, the cracking product which is treated in a main quench tower and the treated gasification product are combined after the main quench tower and the formed mixture is supplied to the recovery unit or to next stage of the recovery unit.

In one embodiment, the treated gasification product is fed to the transfer line and combined with the cracking product to form the feed to the recovery unit. The transfer line can be arranged to transfer the cracking product and the feed to the recovery unit. In one embodiment, the process arrangement comprises at least one transfer line in which the treated gasification product and the cracking product are combined before the recovery unit to form a feed of the recovery unit and which transfers the feed to the recovery unit. In one embodiment, the transfer line transfers the cracking product from a main quench tower to the recovery unit, and the treated gasification product is fed to the transfer line and combined with the cracking product to form the feed to the recovery unit. In one embodiment, the transfer line transfers the cracking product from the steam cracking unit to a main quench tower, and the treated gasification product is fed to the transfer line and combined with the cracking product before the main quench tower. In one embodiment, the process arrangement comprises at least one pipeline to transfer the treated gasification product to the recovery unit or to the transfer line.

In one embodiment, the treated gasification product is pressurized to a pressure of 1-3 bar, in one embodiment a pressure of about 2-3 bar, before combining of the treated gasification product to the cracking product for forming the feed to the recovery unit.

In this context, the recovery unit means any recovery unit, recovery process unit or recovery plant, in which hydrocarbons are separated and/or recovered. The recovery unit may comprise several units, apparatuses or devices, e.g. fractionation, distillation or other separation units, apparatuses or devices or the like or their combinations. In one embodiment, the recovery unit comprises at least one fractionation section, and the feed of the recovery unit is fractionated in the fractionation section of the recovery unit. In one embodiment, the recovery unit comprises at least one cryogenic distillation section in which different fractions are separated by distillation. In one embodiment, the recovery unit comprises a main quench tower, and the cracking product or the treated gasification product and the cracking product are treated in the main quench tower of the recovery unit. In one embodiment, the treated gasification product and the cracking product are fed to the main quench tower or combined before the main quench tower. In one embodiment, the cracking product is fed to the main quench tower, and the treated gasification product is combined with the cracking product after the main quench tower. In one embodiment, the feed may be compressed for the recovery unit or treated in any other way.

In one embodiment, the cracking product is cooled after the steam cracking unit and/or before the recovery unit to a desired temperature. In one embodiment, the process arrangement comprises at least one cooling device for cooling the cracking product. In one embodiment, at least one cooling device is a quench exchanger.

In one embodiment, the treated gasification product is cooled before the recovery unit. In one embodiment, the gasification product is cooled in the quench tower of the gasification unit. In one embodiment, the gasification product further is cooled after the quench tower of the gasification unit. In one embodiment, the gasification product may be cooled before the quench tower of the gasification unit. In one embodiment, the process arrangement comprises at least one cooling device, e.g. a water quench or heat exchanger, in the gasification unit for cooling the gasification product or the treated gasification product. In one embodiment, the cooling device of the gasification unit is a water quench or a heat exchanger. In one embodiment, the treated gasification product may be cooled to temperature of 10-100° C., e.g. 30-50° C., if the treated gasification product is combined with the cracking product treated in a main quench tower after the main quench tower. In one embodiment, the treated gasification product is pressurized to a pressure of more than 1 bar, in one embodiment a pressure of 1-3 bar, if the treated gasification product is combined with the cracking product treated in a main quench tower after the main quench tower.

Possible contaminants of the gasification product may be diluted when the treated gasification product is combined to the cracking product because the cracking product is huge compared to the gasification product. Mass flow of the cracking product may be typically 20+ times higher than mass flow of the treated gasification product. Thus, a contaminant removal is not obligatory.

The method and process arrangement are based on a continuous process.

In one embodiment, the method and process arrangement can be used in a production of olefins, aromatics, e.g. benzene, toluene or other aromatics, other hydrocarbons, polymers, polyolefins or the like, in a production of products from recycled plastic waste, in a recycling of polyolefins back to light olefins, or their combinations.

Thanks to the invention, the treated gasification product from the gasification unit can be transferred safely. The invention enables the safe pipeline transfer of the treated gasification product. Then, the gasification unit can be installed further away the steam cracking unit site, and distance may be hundreds or thousands of meters. The treated gasification product can be transferred from longer distance to the recovery unit. Then an installation site for the gasification unit can be selected flexibly. Further, thanks to the invention, polystyrene can be recycled together with polyolefins. Then, more mixed plastic waste can be recycled efficiently, and polystyrene containing waste can be used as raw material. Further, the integration of the gasification unit to an existing steam cracking unit can be improved.

The method and process arrangement offer a possibility to produce olefins and polyolefins easily, and energy- and cost-effectively. The present invention provides an industrially applicable, simple and affordable way to produce desired products from different plastic-based raw materials. The method and process arrangement are easy and simple to realize in connection with production processes.

Further, the recycling of plastics can be improved by means of the invention. Recycled materials can be treated and utilized easily and effectively. In this process waste materials can be upgraded.

EXAMPLES

FIG. 1 presents some embodiments of the process for producing hydrocarbons from plastic-based raw material by means of a gasification in connection with an integrated process.

In FIG. 1, the integrated process comprises a gasification unit (1) for forming a gasification product (3), a steam cracking unit (2) for forming a cracking product (4), and a recovery unit (8) for recovering hydrocarbons (12).

The process arrangement of FIG. 1 comprises the gasification unit (1) comprising at least one fluidized bed gasifier for gasifying the plastic-based raw material (10) with steam and for forming the gasification product (3). Further, the process arrangement comprises at least one cooling device (5) for cooling at least partly the gasification product (3) for slowing and/or stopping the chemical reactions after the gasification. The gasification product can be cooled rapidly to temperature which is below 640° C. after the gasification in order to stop chemical reactions. Further, the process arrangement comprises at least one quench tower (6) of the gasification unit into which the gasification product (3) is supplied and in which the gasification product is treated and condensable components (9) are removed from the gasification product for forming a treated gasification product (7). Simultaneously the gasification product is cooled in the quench tower (6). Especially tars are separated and removed from the gasification product (3) in the quench tower (6). The condensable components (9) can be recovered. The gasification product (3) may be supplied to the quench tower (6) of the gasification unit via a gas transfer line.

Further, the process arrangement of FIG. 1 comprises means for supplying the treated gasification product (7) and the cracking product (4) of the steam cracking unit (2) to the recovery unit (8) in order to separate and recover desired hydrocarbons (12). Further, the process arrangement comprises a main quench tower (13). The treated gasification product (7) and the cracking product (4) are combined, e.g. in a transfer line, before the main quench tower (13), in which the combined stream of the treated gasification product and the cracking product, i.e. a feed to the recovery unit, is treated. From the main quench tower (13) the stream is supplied to a next section of the recovery unit (8). The process arrangement comprises the transfer line to transfer the cracking product (4) to the recovery unit, and a pipeline to transfer the treated gasification product (7) to the transfer line. In the recovery unit, the feed is fractionated in a fractionation section of the recovery unit, e.g. by cryogenic distillation. Alternatively, the cracking product (4) can be treated in the main quench tower (13) before combining with the treated gasification product (7), and then the treated gasification product is fed to the transfer line after the main quench tower.

If the plastic-based raw material (10) comprises polystyrene and/or styrene, condensable components (9) comprise styrene. Then styrene can be recovered in the quench tower (6) of the gasification unit.

Any suitable devices and equipments can be used in the process of these examples.

The method and process arrangement are suitable in different embodiments for producing olefins, polyolefins and other hydrocarbons from different raw materials.

The invention is not limited merely to the examples referred to above; instead many variations are possible within the scope of the inventive idea defined by the claims.

The invention claimed is:

1. A method for producing hydrocarbons from plastic-based raw material by means of a gasification in an integrated process, in which the integrated process comprises at least one gasification unit for forming a gasification product, at least one steam cracking unit for forming a cracking product, and at least one recovery unit for recovering hydrocarbons, wherein the method comprises steps:

gasifying the plastic-based raw material with steam in the gasification unit using at least one fluidized bed gasifier of the gasification unit to form the gasification product, cooling the gasification product rapidly after the gasification to a temperature of below 640° C. for slowing and/or stopping chemical reactions after the gasification, forming, by the steam cracking unit, the cracking product, supplying the gasification product, which has been cooled to below 640° C., to a quench tower of the gasification unit in which the gasification product is treated and condensable components are removed from the gasification product for forming a treated gasification product, and pressurizing the treated gasification product such that pressure of the treated gasification product is 1-3 bar, combining the treated gasification product and the cracking product of the steam cracking unit before the recovery unit to form a feed of the recovery unit, and supplying the feed formed of the treated gasification product and the cracking product to a main quench tower and supplying the feed to the recovery unit, and separating and recovering, by the recovery unit, desired hydrocarbons from the feed.

2. The method according to claim 1, further comprising recovering the condensable components in the quench tower of the gasification unit.

3. The method according to claim 1, further comprising separating and removing at least tars from the gasification product in the quench tower of the gasification unit.

4. The method according to claim 1, wherein the plastic-based raw material comprises polystyrene and/or styrene, and condensable components comprising styrene are recovered in the quench tower of the gasification unit.

5. The method according to claim 1, further comprising fractionating a feed of the recovery unit in a fractionation section of the recovery unit.

6. The method according to claim 1, wherein the method is for a production of olefins, aromatics, other hydrocarbons, polymers, or poly-olefins, in a production of products from recycled plastic waste, in a recycling of poly-olefins back to light olefins, or their combinations.

7. The method according to claim 1, wherein gasifying the plastic-based raw material with steam in the gasification unit using at least one fluidized bed gasifier of the gasification unit to form the gasification product is carried out at 680-750° C.

8. The method according to claim 1, wherein cooling the gasification product rapidly after the gasification to a temperature of below 640° C. for slowing and/or stopping chemical reactions after the gasification includes cooling the gasification product rapidly after the gasification to a temperature of below 550° C. for slowing and/or stopping chemical reactions.

9. The method according to claim 1, further comprising cooling the treated gasification product such that temperature of the treated gasification product is 10-100° C.

10. The method according to claim 1, wherein forming, by the steam cracking unit, the cracking product is carried out at 750-900° C.

11. The method according to claim 10, further comprising cooling the cracking product such that temperature of the cracking product is 200-250° C.

12. A process arrangement for producing hydrocarbons from plastic-based raw material by means of a gasification in an integrated process, in which the integrated process comprises at least one gasification unit for forming a gasification product, at least one steam cracking unit for forming a cracking product, and at least one recovery unit for recovering hydrocarbons, wherein the process arrangement further comprises the gasification unit comprising at least one fluidized bed gasifier for gasifying the plastic-based raw material with steam and for forming the gasification product, at least one cooling device for cooling the gasification product rapidly after the gasification to a temperature of below 640° C. for slowing and/or stopping chemical reactions after the gasification, the gasification unit further comprising at least one quench tower into which the gasification product, which has been cooled to below 640° C., is supplied and in which the gasification product is treated and condensable components are removed from the gasification product for forming a treated gasification product, at least one device for pressurizing the treated gasification product such that pressure of the treated gasification product is 1-3 bar, means for supplying the treated gasification product and the cracking product of the steam cracking unit to the recovery unit to separate and recover desired hydrocarbons such that the treated gasification product and the cracking product are combined before the recovery unit to form a feed of the recovery unit, and a main quench tower to which the feed of the treated gasification product and the cracking product is supplied and from which the feed is supplied to the recovery unit for the recovery unit to separate and recover hydrocarbons from the feed.

13. The process arrangement according to claim 12, wherein the process arrangement further comprises at least one transfer line in which the treated gasification product and the cracking product are combined before the recovery unit to form a feed of the recovery unit and which transfers the feed to the recovery unit.

14. The process arrangement according to claim 12, wherein the process arrangement further comprises at least one water quench or heat exchanger as the cooling device for cooling the gasification product after the gasification.

15. The process arrangement according to claim 12, wherein the fluidized bed gasifier is selected from a bubbling fluidized bed gasifier or a circulating fluidized bed gasifier.

16. The process arrangement according to claim 12, wherein the gasification unit carries out the gasification of the plastic-based raw material with steam at 680-750° C.

* * * * *